US 6,645,469 B2

(12) United States Patent
Pera

(10) Patent No.: US 6,645,469 B2
(45) Date of Patent: Nov. 11, 2003

(54) METHOD FOR DISPENSING S-ADENOSYL-METHIONINE IN A MICRO FINE POWDERED FORM BY INHALATION

(76) Inventor: Ivo E. Pera, 1400 St. Charles Pl., Pembroke Pines, FL (US) 33026

( * ) Notice: Subject to any disclaimer, the term of this patent is extended or adjusted under 35 U.S.C. 154(b) by 0 days.

(21) Appl. No.: 10/085,404

(22) Filed: Feb. 28, 2002

(65) Prior Publication Data

US 2002/0122774 A1 Sep. 5, 2002

(30) Foreign Application Priority Data

Mar. 1, 2001 (EP) .......................................... 01125055.2

(51) Int. Cl.$^7$ ............................ A61K 9/12; A61K 9/14; A61K 9/72
(52) U.S. Cl. ...................... 424/46; 424/489; 424/499; 514/23; 514/29; 514/54; 514/62
(58) Field of Search ...................... 424/46, 499, 489; 514/23, 29, 54, 62

(56) References Cited

U.S. PATENT DOCUMENTS 5,872,104 A  *  2/1999  Vermeulen et al. ........... 514/29
2002/0110599 A1  *  8/2002  Auweter et al. ............. 424/499

* cited by examiner

Primary Examiner—Michael G. Hartley
Assistant Examiner—Mina Haghighatian
(74) Attorney, Agent, or Firm—Malin, Haley & DiMaggio, P.A.

(57) ABSTRACT

A method is provided for dispensing dry micro powdered SAMe compositions (or SAM or AdoMet), an abbreviation for S-adenosyl-methionine, wherein SAMe, as active ingredient is contained in an amount effective to achieve its intended purpose, with a membrane permeation enhancer such as lactose. The compound is administered via a conventional dry powder inhaler to deliver said the compound into the subject's respiratory tract in order to enhance prophylactic and therapeutic effects of SAMe, without the Aid or use of propellants, chlorinated, halogenated, gases, liquids, vapors, aerosol, spray, vaporization, or any other similar devices or delivery methods.

15 Claims, No Drawings

METHOD FOR DISPENSING S-ADENOSYL-METHIONINE IN A MICRO FINE POWDERED FORM BY INHALATION

This application claims the benefit of and priority to European Patent Application No. EP 01125055.2, filed Mar. 1, 2001.

DESCRIPTION

1. Technical Field

The present invention relates generally to the technical sector of chemistry and pharmacology and particularly to a new method for dispensing a medicine. It doesn't consist of a therapeutic treatment, since the therapeutic function of the S-Adenosilmetionina (SAMe) is already known, but it discloses a new use, by means of a method for dispensing it through the respiratory tract.

2. Background Art

The assimilation of an adequate quantity of physiologically important S-Adenosylmethionine is essential to the health of people. Failure of the body to assimilate the necessary amount of such SAMe which acts as a methyl donor in over 35 methylation reactions involving DNA, proteins, phospholipids and catechol and indole amines, that can lead to the improvement of the biochemical reactions of the body functions and the metabolic processes as well as to the prevention or cure of variety of diseases and associated symptoms. SAMe=S-Adenosyl-L-methionine, S-(5'-deoxyadenosine-5')-methionine, active methionine, active methyl, abbreviated as S-Ado-Met, SAM: a reactive sulfonium compound which is the most important methylating agent in cellular metabolism (transmethylation). It is formed by activation of L-methionine with ATP: Met+ATP–SAM+$PP_1$+$P_1$. The adenosine residue of the ATP is transformed to the methionine.

The transmethylation reaction produces, in addition to the methylated product, S-adenosyl-L-homocysteine: systematic name S-(5'deoxyadenosine-5')-homocysteine. It may be reconverted to SAM after cleavage into adenosine and L-homocysteine. L-Homocysteine is the substrate of dimethylthetin-homocysteine methyltransferase. SAMe controls virtually all body functions in man beginning with sugar metabolism and fatty acid metabolism and extending to the immune system and even mental stability, through SAMe mediated modification of a number of critical neurotransmitters and hormones. Not surprisingly, SAMe also controls aging of the organism. Hence, virtually all diseases and/or disorders associated with aging, such as diabetes, atherosclerosis, arthritis and Alzheimer's disease, are caused by abnormal perturbations of the SAMe pathways.

SAMe has been clinically proven to promote joint health and support emotional wellbeing.

SAMe is one of the most vital links to health known today in maintaining not only health but in preventing diseases. SAMe most significant claims include efficacy in treating depression, osteoarthritis, cirrhosis of the liver, fibromyalgia, cancer, cystic fibrosis, ALZHEIMER's and PARKINSON's diseases.

The importance of this reaction in maintaining health cannot be overemphasized. Everything from activating or deactivating enzymes to converting the coded messages in our DNA to actual proteins involves methylation reactions, and therefore SAMe.

Many scientists have known for years that most of us don't get all the vitamins we need from our food and that the RDA levels of many vitamins are absurdly low. We also know that the levels of folate and SAMe in the blood of many people are too low for their optimum health, mental and physical. Likewise, we know that homocysteine levels in the upper half of the normal range are a risk factor for many diseases, including hearth attack.

Unfortunately today is considered normal to have a heart attack even at a young age, but today thank to SAMe many, if not most heart attacks and strokes are almost entirely preventable! In fact, the basic process of vascular disease, arteriosclerosis and athrosclerosis is largely preventable.

SAMe is a naturally occurring molecule that is part of all living cells, and affect so many different aspects of human biology and pathology being a metabolic helper that is produced during methylation and facilitates nearly all methylation reactions in your body.

As one of the primary methyl group donors, SAMe is extremely important and historically unappreciated. One of its many roles is methylating DNA. When DNA is properly laced with methyl groups, your cells are protected form the abnormal expression of DNA, a behavior associated with disease and aging. Aside from this sole in DNA methylation, SAMe also acts as a natural antidepressant, possibly through its role in creating the neurotransmitter melatonin.

Clinical studies have long shown oral intake of SAMe to have antidepressant effects. Recent clinical studies have also shown it to be very effective in maintaining a healthy liver, and it is even effective in people who already have alcoholic liver cirrhosis. However, perhaps its greatest potential in preventing or delaying serious age-related disease lies in its ability to regulate plasma homocysteine metabolism. High levels of homocysteine, a sulfur-containing amino acid, have been highly correlated with the onset of cardiovascular and cerebrovascular disease. One very important way your body gets rid of homocysteine is to put a methyl group on it and form methionine, which is not harmful. SAMe is a major contributor to this process, and it does this by methylating a substance called tetrahydrofolate, which in turn methylates homocysteine to methionine, SAMe taken orally has been shown to increase levels of methylated tetrahydrofolate in humans, thus potentially decreasing their risk of cerebrovascular (stroke) and cardiovascular disease. This seems logical, when considered with the fact that patients with coronary artery disease have been shown to have significantly lower levels of SAMe than similar individuals without coronary artery disease.

SAMe may also have a role in cancer prevention. In certain types of cancer, reduced methylation of DNA may contribute to loss of the control on genes that control normal cell division. In human, low methylation of DNA has been observed in colorectal cancers and in their adenomatous polyp precursors. Low dietary folate and methionine and high intake of alcohol may reduce levels of SAMe, which as noted previously is required for DNA methylation. Therefore, oral supplementation of SAMe may be prophylactic in individuals at risk for these types of cancers.

Improving the methylation process in the body, SAMe will:

- reduce the risk of hearth disease
- reduce the risk of cancer
- slow or reduce the risk of age-related diseases, including Alzheimer's disease, Parkinson's and Arthritis
- reduce the risk of a host of other diseases and conditions including birth defects, liver disease
- improve the mood improve existing ailments such as herpes, diabetes, depression, poor digestion and fatigue control the weight and increase mass.

SAMe may be administered by different methods. The various methods include oral, rectal, sublingual or buccal, parental inhalation, topical, etc. The choice of method depends upon both convenience and necessity. Obviously, drug substances are most frequently administered orally for access to the systematic circulation by means of solid dosage forms, such as tablets and capsules. Oral administration does not always give rise to sufficiently high plasma concentrations to be effective. Some drugs are absorbed unpredictably or erratically. Patients occasionally have an absorption malfunction.

Fillers and binders comprise the bulk of the contents in SAMe tablets to which most people exhibit adverse side effects, such as headaches, rashes, hives, itching, and upset stomach, while the same vitamin doses when taken as the pure vitamin by injection without fillers or binders does not produce these side effects.

Several doctors who use in their practice, drugs via oral administration have observed many such undesirable reactions, including headache, arthritis, joint pain, chronic fatigue, depression, personality changes, gout attacks, and even chronic earaches and infection in children. It has been discovered that the allergic reactions are generally to table fillers and binders, not to the drugs themselves (though it is recognized that even vitamins cause problems in excessive doses).

In clinical research, it has been confirmed that 8 to 10 percent of the tested, clinical population is allergic to corn starch and other corn products and about another 10 percent to soy products. These allergies can be sufficiently severe to produce very unpleasant symptoms when SAMe tablets using these fillers and binders are taken.

Great interest has been recently developed to the highly effective therapeutic usefulness of the Dry Micro-powdered Inhalation Therapy. Such forms of administration offer many advantages to the patient. It is well known that many drugs are capable of being absorbed rapidly by inhalation.

The method of application of the present inhalation process makes possible delivering the same into the respiratory tract of humans in order to enhance the propylactic and therapeutic effects of such same composition to decrease or prevent diseases, therefore through dispensing such SAMe into the respiratory tract, and in accordance with my numerous laboratory test, I have been successful to confirm specific preventive effects, in the development of numerous diseases.

Accordingly one purpose of my invention is to provide a dry micro fine powder compound of SAMe for local administration by inhalation. This system offers the advantage of (1) local administration of small doses of the above SAMe with protective effect against many diseases, in a "on-pharmacological" and spontaneous way and (2) concomitant distribution of such SAMe in the respiratory tract, which are more effectively absorbed and retained in the human body with specific preventive effect.

The SAMe Inhalation therapy of the present invention offers the following major advantages:

The inhaled SAMe composition is transmitted to the site where it is required, namely through the respiratory system, where it becomes far more effective and with greater speed than any orally taken medication.

Due to the fact that the SAMe is transmitted directly into the respiratory system only one tenth of the quantity is required compared with any other form of administration, with the results that undesirable side-effects are rare.

To decrease or prevent many diseases, my invention relates to a method for delivering SAMe into the respiratory tract of humans, in order to enhance the prophylactic and therapeutic effects of same.

A further object of the present invention is to administer in a dry microfine powdered form by inhalation as a prevention means or as a medical treatment.

In administering SAMe for inhalation in dry powder form to deliver the same into systemic circulation via the respiratory tract, the adsorption is virtually immediate, since the alveolar and vascular epithelial membranes are quite permeable, blood flow is abundant and there is a very large surface for adsorption.

Dry Powder Inhalers (DPIs) deliver their dose on the breath of the patient, consequently, the pattern of delivery is different from that of the aerosol inhalers. The DPIs are extremely simple and foolproof, especially with respect to accuracy of dosage and accurate placement of the drug. For this reason, the DPIs are ideal vehicles to dispense SAMe to the respiratory tract, and are preferable to the aerosol inhaler, particularly over oral preparations for several reasons. An example of a dry powder Inhalers which can be utilizes to deliver dry powder drugs is shown in my Patents and Patents pending for inhaler devices. Other conventional dry powder inhalers may also be utilized and are considered within the scope of the invention.

After the SAMe has been inhaled immediately it is absorbed into the bloodstream and then pumped to all organs in the body, instead of if a tablet or a capsule is ingested, one must take a relatively large amount of an oral drug to deliver a small dose to a selected target organ, such as the lungs. The drug is also transported to other organs where it is not needed and may cause unwanted side effects. The shortcomings of oral drugs are overcome by the present invention which delivered the SAMe directly to the target organ.

The lung is considered to be one of the more effective non-invasive routes of administration to the systemic circulation. Numerous types of dry micro fine powdered SAMe formulations can be used to treat a variety of conditions that accompany many different diseases.

Therefore, to acquire full health protection, it is may be necessary to fortify the body with SAMe as the latest scientific findings from all over the world confirm, the potential of the SAMe to provide health benefits which may include the following:

increased protection from many forms of cancer;

stronger defenses against cardiovascular disease, such as atherosclerosis, heart attacks, and strokes, liver disorders, kidney failure, rheumatoid arthritis, osteoarthritis, osteoporosis, depression and other psychiatric disorders, type II diabetes and complications of diabetes, fibromylagia, chronic fatigue syndrome, Alzheimer's disease, cognitive decline, multiple sclerosis;

a delay in the onset of premature aging;

a more powerful immune system;

a decreased risk of early Parkinson's disease and other chronic diseases, as well as a host of other major health advantages.

The SAMe may also cure anxiety disorders, amebic dysentery, anosmic aplasia, analgesic, cholecystitis, cushing syndrome, menstruation and menopause distress, gastritis, crohn's disease, leukemia, lymphopathy, obesity.

Many physicians have been taking SAMe for years, even before the weight of scientific authority shifted so heavily in the SAMe direction.

The determination of quantitative daily human requirements for SAMe could be made if it were possible to correlate known nutrient intake with specific biological responses in precisely controlled studies, the daily amount suggested is:

up to 150 mg. per day to be inhaled three times (morning, noon and evening).

Though the benefits of SAMe is well documented, methods of delivering the vitamins to the respiratory area of a patient have been far from superior, but unfortunately SAMe never has been tested, dispensed or even suggested, until the present invention to be administered in a microfine powder form by inhalation.

Thus, what is needed in the art is method for dispensing SAMe within a patient which will allow for maximum benefits from such medicine for therapeutic treatment of diseases through the respiratory tract.

SUMMARY OF THE INVENTION

It is therefore, to the effective resolution of the aforementioned problems and shortcomings that the present invention is directed.

The present invention provides a method is provided for dispensing dry micro powdered SAMe compositions (or SAM or AdoMet), an abbreviation for S-adenosylmethionine (all collectively referred to as SAM for purposes of the disclosure and claims), wherein SAMe, as active ingredient is contained in an amount effective to achieve its intended purpose, with a membrane permeation enhancer such as lactose. The compound is administered via a conventional dry powder inhaler to deliver said the compound into the subjects respiratory tract in order to enhance prophylactic and therapeutic effects of SAMe, without the aid or use of propellants, chlorinated, halogenated, gases, liquids, vapors, aerosol, spray, vaporization, or any other similar devices or delivery methods.

Thus, the method dispenses SAMe in dry, powdered form by inhalation as prevention or for medical treatment for several diseases. Preferably, SAMe is in a dry, ultra silky, micro, fine powdered form. Many ingredients can be added as membrane permeation enhancers to the SAMe formulation to increase their barrier permeability, but the preferred one and the most effective are lactose and glutathione.

The present invention method delivers the dry, micro fine powder in one step through the respiratory tract and without the aid or use of aerosols, liquids, vapors, gases, vaporization or any other similar or like devices or delivery methods.

Preferably, the dry fine powder compound consist of a plurality of particles which are between approximately 0.1 micrometer and approximately 10 micrometer in size, though such is not considered limiting and other sizes and ranges can be used and are considered within the scope of the invention.

The principal purpose of the present invention is to use any inhaler known in the art to dispense a dry, powdered compound consisting of SAMe, lactose and/or antioxidants through the mucosal linings of tracheobronchial tree and the lungs, to prevent or cure depression and other diseases.

The invention relates to a novel method of supplementing, through the respiratory tract, essential SAMe by the use of a drug powder inhaler which allows their immediate assimilation, compensating for certain absorptive disorders and side effects.

A further object of the present invention is a method of dispensing SAMe in a microfine powder form which is used to treat or prevent diseases including but not limited to liver disorders, kidney failure, arthritis, depression, fibromyalgia, Alzheimer and Parkinson's diseases, atherosclerosis, heart attack, diabetes, obesity, and cancer.

The essential SAMe composition, when administered through the respiratory tract, is directly available for absorption into the system without competition from other medications. When the SAME is dispersed by inhalation through the respiratory tract, is instantaneously assimilated by the plasma and is immune to possible deterioration or interaction of prescribed medicaments and aspirin and/or alcohol.

In recent years, a great deal of scientific literature has been published, reporting the extraordinary effects of SAME. It is not easy to summarize in a few pages the numerous properties of these remarkable substances, the evidence accumulated to date including the studies of the present invention, leave little doubt that SAMe exert favorable effects on many types of diseases and, in fact, there is published evidence demonstrating that the SAMe exert a direct effect on preventing or curing several diseases particularly depression.

Thus, it is an object of the invention to provide a composition and method for selectively supplementing the essential SAMe in the diet of people and for facilitating its absorption for the prevention of diseases.

It is also an object of the invention to correct the deficiency of SAMe in people due to the excessive homocysteine activity which pose one of the greatest single threats to the public health and to prevent and/or eliminate the symptoms of those deficiencies. By so doing, deficiencies can be therapeutically eliminated without the need for massive doses of drugs.

A further object of the invention is to administer SAMe in a dry, powdered form by inhalation as a prevention means or as a medical treatment.

In accordance with these and other objects which will become apparent hereinafter, the instant invention will now be detailed in the following pages.

DETAILED DESCRIPTION OF THE INVENTION

The present invention relates to employing a dry powder inhalation device for delivering SAME in a microfine powdered form into systemic circulation via the respiratory tract. Absorption is virtually as rapid as the drug can be delivered into the alveoli of the lungs, since the alveolar and vascular epithelial membranes are quite permeable, blood flow is abundant and there is a very large surface for adsorption.

Aerosol delivered from pressure-packaged, metered-dose inhalers (MDIs) are composed of the drug, additives, and propellants. The high vapor pressure of propellant supplies the force necessary to generate aerosol droplets.

Aerosol of non-volatile substances may also be administered by inhalation, but the route is infrequently used for delivery into the systemic circulation because of various factors that contribute to erratic or difficult-to-achieve blood levels. Whether or not an aerosol reaches and is retained in pulmonary alveoli depends crucially upon particle size; particles greater than 1 micrometer in diameter tend to settle in the bronchiole and bronchi, whereas particles less than 0.5 micrometer fail to settle and are mainly exhaled. Aerosols are mostly employed when the purpose of administration is an action of the drug upon the respiratory tract itself.

Dry powder inhalers (DPIs) deliver their dose on the breath of the patient, consequently, the pattern of delivery is different from that of the metered dose inhalers. The DPI is extremely simple and foolproof, especially with respect to accuracy of dosage and accurate placement of the drug. For this reason, the DPIs are ideal vehicles to dispense SAMe to the respiratory tract, and are preferable to the aerosol inhaler, particularly over oral preparations for several reasons. An example of a dry powder inhaler which can be utilized to deliver a dose of microfine dry powder composition is shown in my U.S. Pat. Nos. 5,669,378 and 5,944,012 which are incorporated herein by reference. Other conventional dry powder inhaler may also be utilized and are considered within the scope of the invention.

The present invention provides a method for dispensing a dry, powdered compound consisting of SAMe and lactose using a DPI, which can be inhaled into the lungs to produce a faster onset of action without any side effects. This new method of dispensing antioxidant vitamins through the respiratory tract is breath-activated, meaning the patient does not have to coordinate inhalation with activating the inhaler and does not inhale cardio-toxic gas propellants into the lung.

The lung is considered to be one of the more effective non-invasive routes of administration to the systemic circulation. A number of different dry, powder SAMe formulation can be used to treat a variety of conditions that accompany many different diseases.

SAMe as an extraordinary natural chemical is produced by a healthy body each day being synthesized in the liver to perform many of its basic functions, including regeneration of its own tissue.

SAMe is the body's most important metabolic helper that defend the body from the damaging effects of uncontrolled damage of too much homocysteine in the body causing untold stroke or hearth attack, and damage the DNA in our cells which control growth, stimulate the immune system, and prevent or reduce the risk of cancer, liver disease, premature aging and depression, as well as protecting our bodies from harmful toxins, promoting optimum health and well being.

Excess of homocysteine have been shown to an extremely toxic substance that build up in cells to develop cancer, bacterial and viral infections, stroke, arthritis, hearth attack and being a major factor in causing many more diseases.

In recent years, much scientific research has been done and the validity of using SAMe can dramatically improve health and to prevent and/or cure diseases and to bolster the immune defenses against excessive build up of homocysteine due to its powerful damaging properties.

The method of application of the present invention makes possible delivering the SAMe into the respiratory tract of humans in order to enhance the prophylactic and therapeutic effects of such SAMe to decrease the risk of diseases. Thus, dispensing SAMe into the respiratory tract in accordance with our numerous laboratory tests, we have been successful in confirming the specific preventive effects in the several diseases.

Accordingly, one purpose of this invention is to provide a dry, powder compound of SAMe for local administration by inhalation. This system offers the advantages of (1) local administration of small doses of the above SAMe with protective effect against diseases, in a "non-pharmacological" and spontaneous way; and (2) concomitant distribution of such SAMe in the respiratory tract, which will be more effectively absorbed and retained in the human body with specific preventive effect. When SAMe levels are increased, some amazing things start to happen, many people have found relief from such debilitating illness as depression, liver diseases and many more.

While the present invention has been described with reference to specific medical procedure for dispensing SAMe by inhalation, it will be understood by those skilled in the art that various other formulation with SAMe can be used without departing from the spirit of the invention and rights to such alternatives are particularly reserved, especially those which fall within the scope of the appended claims.

Thus, in use SAMe and a membrane permeation enhancer such as saccharide, glycosides, etc., such as lactose, sucrose, mannitol or sorbitol, magnesium stearate, and/or one or more water soluble antioxidants, all formed into a dry powder compound and kept together, prior to use, by conventional means, such as a capsule member. The capsule member, containing the dry powder compound is disposed into a conventional dry powder inhaler. When the dry powder compound is desired, the inhaler is activated causing the compound to be delivered to the subject's respiratory tract in order to enhance prophylactic and therapeutic effects of the SAMe. Other ingredients can also be included within the dry powder SAMe compound. Thus, the dry powdered compound is inhaled into the subject's lungs to produce a faster onset of action. When administered through the respiratory tract, SAMe is directly available for absorption into the subject's system without competition from other medications. When SAMe is dispersed by inhalation through the respiratory tract, they are instantaneously assimilated by the plasma and are immune to possible deterioration or interaction of prescribed medicaments and aspirin and/or alcohol.

The present invention method delivers the dry, micro fine powder in one step and without the aid or use of aerosol(s), propellants, chlorinated, halogenated, gas(es), liquids, spray, vaporization or any other similar or like devices or methods.

Preferably, SAMe formulation can be in a dry, ultra silky, micro fine powdered form. The dry powder compound preferably consist of a plurality of particles which are between approximately 0.1 micrometer and approximately 10 micrometers in size, though such is not considered limiting.

The relative amounts of the SAMe composition can vary a great deal. For example, the amount of SAMe in the inhaling composition will depend on a variety of factors, including the disease to be treated, the desired effect, possible adverse reactions and other factors within the particular knowledge of the patient and physician. The amount of enhancer present in the composition will similarly depend on a number of factors, e.g. on the depth of penetration desired through the respiratory system, the strength of the particular permeation enhancer duly selected, and the like.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A method for dispensing S-Adenosylmethionine (SAMe) in the form of a dry micro fine powder directly to a human subject by inhalation, said method comprising the steps of:

(a) forming a dry micro fine powder composition comprising S-adenosylmethionine as an active ingredient; and (b) dispensing, upon breath activation by the human subject, of an effective amount of the dry micro fine powder SAMe composition directly into the mouth of the subject by a dry powder inhaler to allow said composition to reach the subject's respiratory tract without the use of propellants, chlorinated, halogenated, gas(es), liquids, sprays aerosol(s) or vaporization;

wherein the composition is directly administered through inhalation to the subject's respiratory tract in a dry micro fine powder form.

2. The method for dispensing of claim 1 wherein said dry micro fine powder composition further consist of a membrane permeation enhancer.

3. The method for dispensing of claim 2 wherein said membrane permeation enhancer is lactose and/or glutathione.

4. The method for dispensing of claim 1 wherein said method allows for delivery into the subject's respiratory tract SAMe, in order to enhance prophylactic and therapeutic effects of the SAMe.

5. The method of claim 1 wherein said dry micro fine powder composition consist of a plurality of particles which are between approximately 0.1 micrometer and approximately 10 micrometer in size.

6. The method of claim 2 wherein said membrane permeation enhancer is magnesium stearate.

7. The method for dispensing of claim 2 wherein said membrane permeation enhancer is lactose and/or one or more water soluble antioxidants.

8. A method for dispensing a SAMe composition in a dry micro fine powder form directly to a human subject with the use of a conventional dry powder inhaler, said method comprising the steps of:

(a) forming a dry micro fine powder SAMe composition with or without a membrane permeation enhancer; and (b) dispensing, upon breath activation by the human subject, of an effective amount of the dry micro fine powder SAMe composition directly into the mouth of the subject with the dry powder inhaler to allow said composition to reach the subject's respiratory tract, without the aid or use of propellants, chlorinated, halogenated, gas(es), liquids, spray, aerosol(s) or vaporization;

wherein the composition is directly administered through inhalation to the subject's respiratory tract in a dry micro fine powder form.

9. The method for dispensing of claim 8 wherein said method allows for delivery of a SAMe composition into the subject's respiratory tract in order to enhance prophylactic and therapeutic effects of said SAMe.

10. The method for dispensing or claim 8 wherein said membrane permeation enhancer is lactose and/or one or more water soluble antioxidants.

11. The method of claim 8 wherein said dry micro fine powder compound consist of a plurality of particles which are between approximately 0.1 micrometer and approximately 10 micrometer in size.

12. The method of claim 8 wherein said membrane permeation enhancer is magnesium stearate.

13. The method for dispensing of claim 8 wherein said membrane permeation enhancer is lactose and/or glutathione.

14. A method for improving the effectiveness of S-Adenosylmethionine (SAMe) when administered to a human subject, said SAMe composition in a dry micro fine powder form, said method comprising the step of administering to a subject an effective dose of a dry micro fine powder composition with or without lactose, and/or antioxidants via a conventional dry powder inhaler, upon breath activation by the human subject, to deliver said SAMe directly into the subject's respiratory tract, without the use of gas(es), liquids, spray, aerosol(s) or vaporization, in order to enhance prophylactic and therapeutic effects of the SAMe; wherein the composition is directly administered through inhalation to the subject's respiratory tract in a dry micro fine powder form.

15. The method of claim 14 wherein said dry micro fine powder composition consist of a plurality of particles which are between approximately 0.1 micrometer and approximately 10 micrometer in size.

* * * * *